United States Patent [19]

Patel

[11] 4,419,094
[45] Dec. 6, 1983

[54] SUPRAPUBIC CATHETER SYSTEM

[75] Inventor: Bhupendra C. Patel, Elgin, Ill.

[73] Assignee: The Kendall Company, Boston, Mass.

[21] Appl. No.: 271,292

[22] Filed: Jun. 8, 1981

[51] Int. Cl.³ ............................................. A61M 11/00
[52] U.S. Cl. ..................................... 604/93; 604/115;
604/158; 604/161
[58] Field of Search ............... 128/349 B, 349, 132 D,
128/347, 348, 350 R, 294, 295, 329 R, 329 A,
207.17, DIG. 26; 604/158, 159, 283, 161, 163,
162, 164, 165, 166, 170, 171, 93, 95, 115, 116,
117, 118

[56] References Cited

U.S. PATENT DOCUMENTS

| | | | |
|---|---|---|---|
| 2,693,186 | 11/1954 | Riker et al. | 128/218 F |
| 2,922,420 | 1/1960 | Cheng | 604/158 |
| 3,860,006 | 1/1975 | Patel | 128/347 |
| 4,029,103 | 6/1977 | McConnell | 128/DIG. 26 |
| 4,149,539 | 4/1979 | Cianci | 128/DIG. 26 |
| 4,187,848 | 2/1980 | Taylor | 128/247 |
| 4,275,728 | 6/1981 | Merry | 604/165 |
| 4,316,461 | 2/1982 | Marais et al. | 128/DIG. 26 |
| 4,326,520 | 4/1982 | Alley | 604/159 |

FOREIGN PATENT DOCUMENTS 564456 11/1932 Fed. Rep. of Germany ...... 128/329

*Primary Examiner*—C. Fred Rosenbaum
*Assistant Examiner*—J. L. Kruter
*Attorney, Agent, or Firm*—Powell L. Sprunger

[57] ABSTRACT

A suprapubic catheter system comprising, a puncture member comprising an elongated needle. The system has a catheter assembly comprising an elongated catheter having a distal end for placement in a patient, a proximal end, and a lumen to receive the needle. The catheter assembly has a stabilizer comprising a plate extending on opposed sides of the catheter, with the plate having an opening to slidably receive the plate on the catheter, a pocket containing a anti-septic agent, and the assembly has a device for selectively locking the stabilizer at a desired position on the catheter.

6 Claims, 11 Drawing Figures

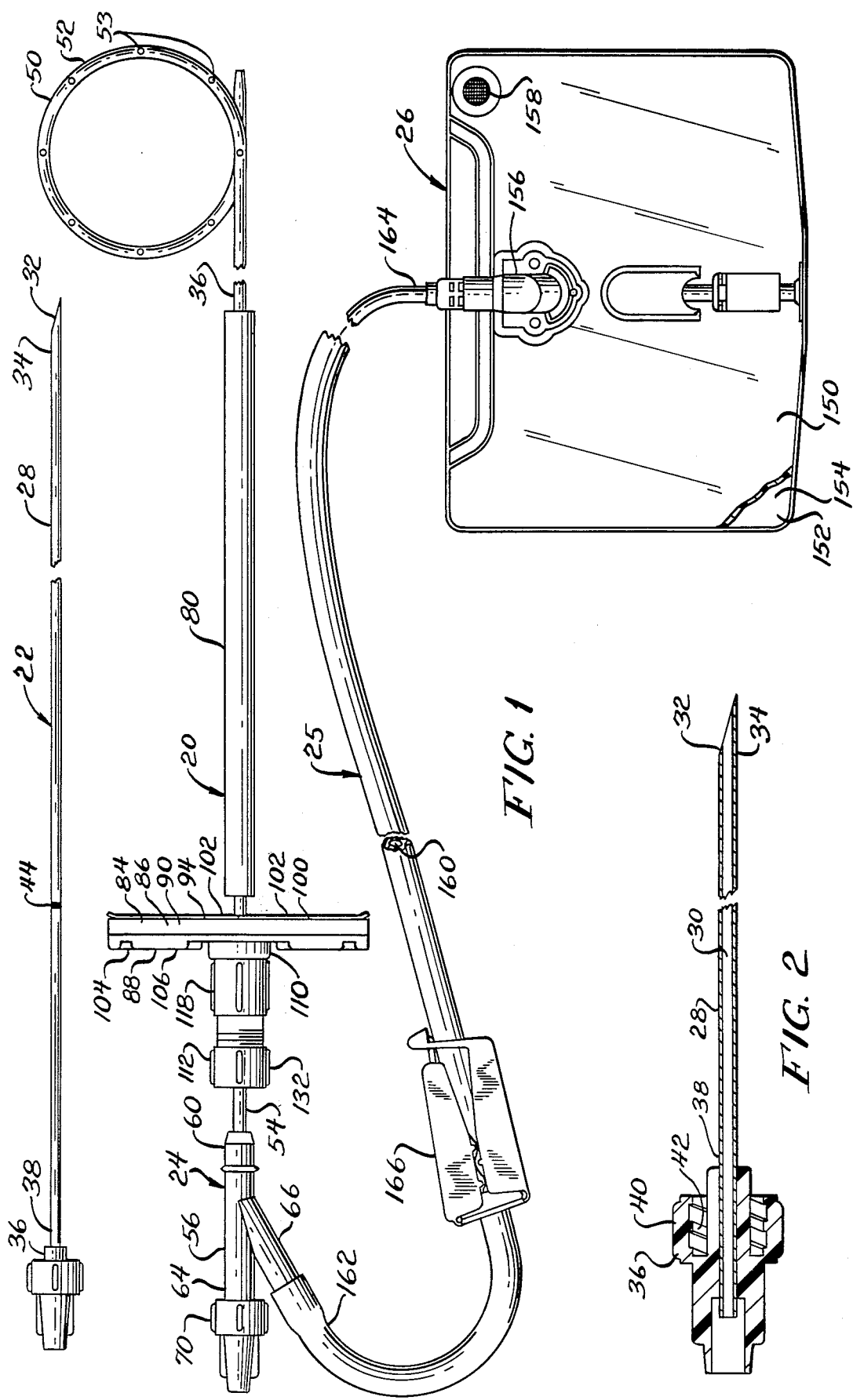

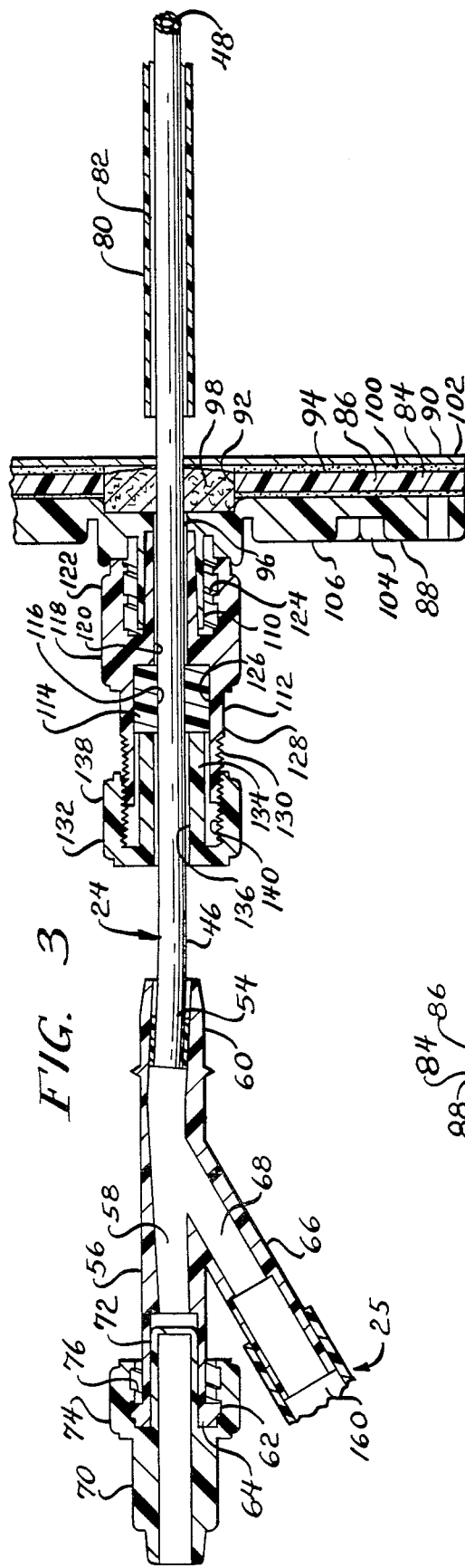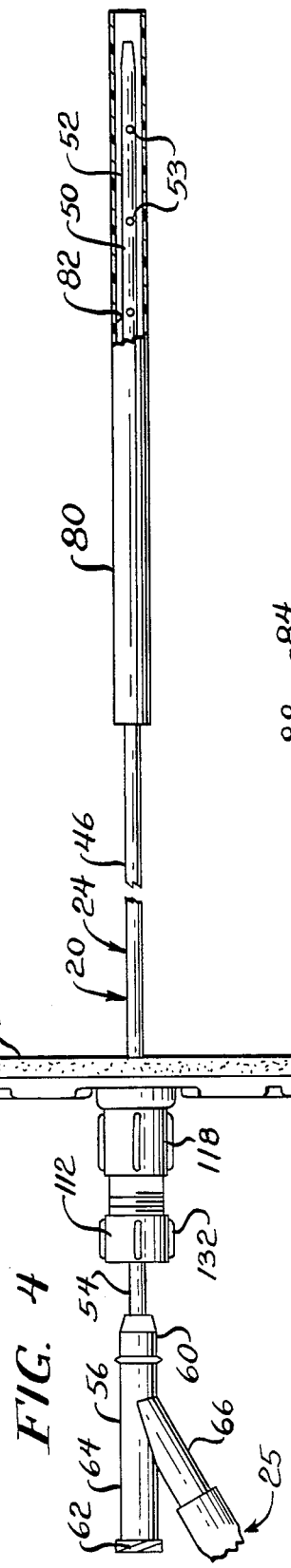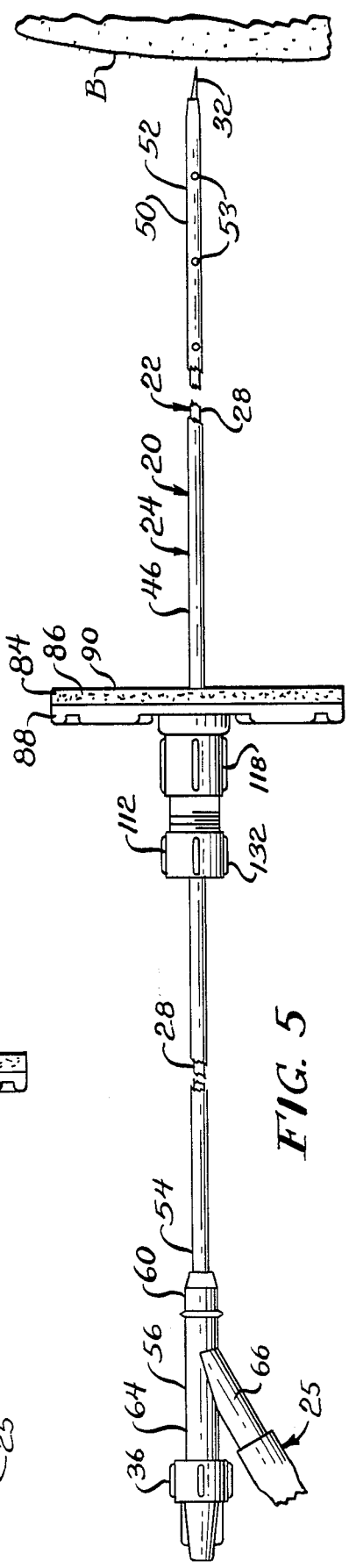

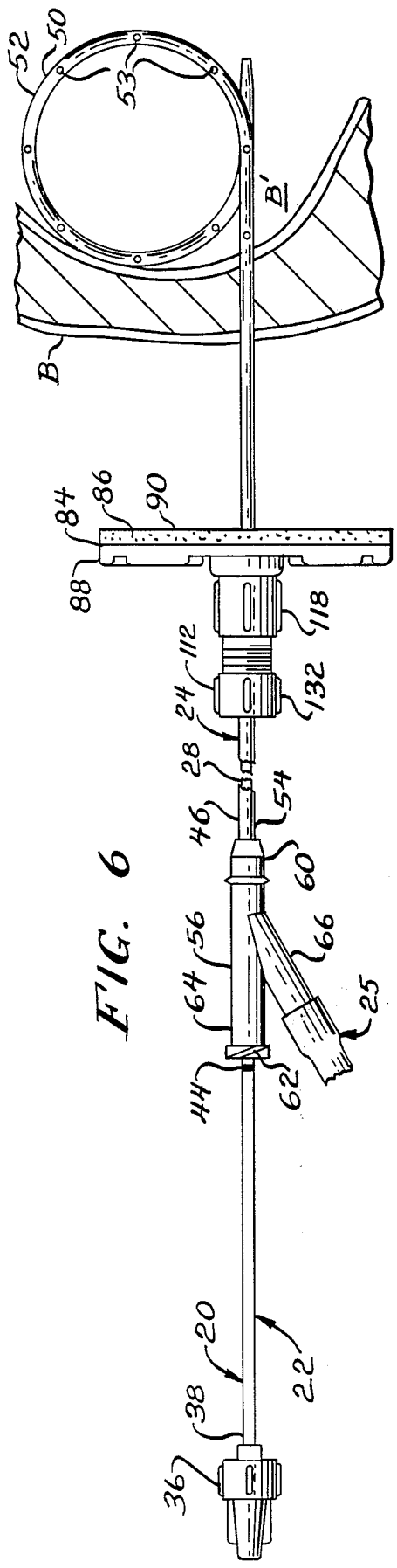
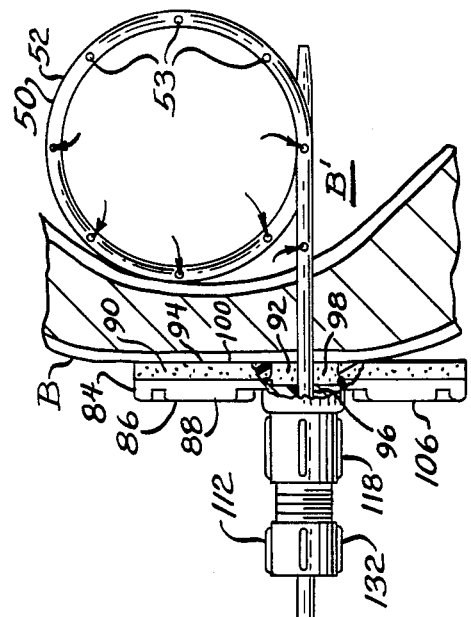
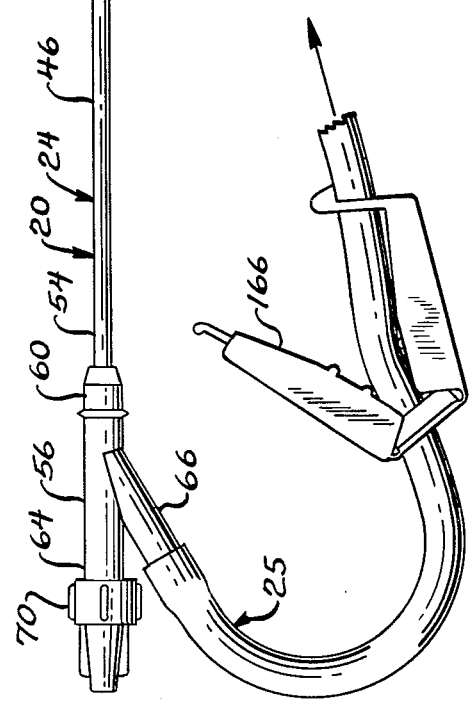
FIG. 6
FIG. 7

SUPRAPUBIC CATHETER SYSTEM

BACKGROUND OF THE INVENTION

The present invention relates to suprapubic catheter systems.

Patients are commonly catheterized with urinary or Foley catheters in which the catheter is passed through the urethra of a patient until a distal end of the catheter is located in the patient's bladder. During catheterization with a urinary catheter, urine drains from the bladder through the catheter, and through a drainage tube attached to a proximal end of the catheter to a drainage bag for collection therein. In suprapubic systems, a catheter is passed through the abdominal wall of the patient until a distal end of the catheter is located in the bladder. During catheterization with a suprapubic catheter, urine drains from the bladder through the catheter, through a drainage tube connected to a proximal end of the catheter to a drainage bag for collection therein.

There are important advantages of the suprapubic catheter over the urinary catheter. First, the incidence of infection in the suprapubic systems is much less than that in urinary catheters. Second, if surgery has taken place in the region of the urethra, it is desirable to keep the catheter from the surgical area to promote healing. Third, urinary catheters prevent normal voiding by the patient, while the suprapubic systems permit voiding once the drainage tube in the suprapubic system is closed. Hence, in suprapubic systems the physician may readily determine whether the patient is ready to void naturally, while in urinary catheter systems the catheter must be removed from the patient to achieve this result. Finally, the suprapubic systems are more comfortable for the patient than urinary catheters, and the suprapubic systems increase the mobility of the patient.

SUMMARY OF THE INVENTION

A principal feature of the present invention is the provision of an improved suprapubic catheter system.

The system of the present invention comprises, a puncture member comprising an elongated hollow needle, and a hub attached to a proximal end of the needle. The system has a catheter assembly comprising an elongated catheter having a distal end portion in the form of a coil for placement in a patient, a proximal end, and a lumen to receive the needle. The assembly has a Y-connector attached to the proximal end of the catheter, with the connector having a bore extending therethrough to receive the needle, and a sidearm having a lumen communicating with the bore. The assembly has a stabilizer comprising a plate extending on opposite sides of the catheter, with the plate having an opening to slidably receive the plate on the catheter. The assembly also has means for selectively locking the stabilizer at a desired position on the catheter. The puncture member has an indicating mark on the needle at a location spaced a distance from the hub approximately equal to the length of the coil of the catheter. The system has a drainage receptacle having a chamber, and a conduit having a lumen, with an upstream end of the conduit connected to the sidearm of the connector, and with a downstream end of the conduit connected to the receptacle.

A feature of the present invention is that after puncture through the abdominal wall by the system, the catheter may be moved distally on the needle until the indicating mark is exposed on the needle.

Another feature of the invention is that the indicating mark indicates when the coil of the catheter is located in the patient's bladder.

Yet another feature of the invention is that the stabilizer may have a slot on a proximal surface of the plate to receive the catheter and secure it in place after placement of the system.

A further feature of the invention is that a distal surface of the stabilizer may have adhesive for securing the plate to the patient's body.

A further feature of the invention is that the stabilizer may have a pocket on a distal surface of the plate extending around the opening to receive an antiseptic agent for placement against the patient's body in order to reduce the possibility of retrograde migration of bacteria.

Yet another feature of the invention is that the stabilizer may have a plurality of spaced apertures for securement of the plate to the patient's body through use of sutures.

Still another feature of the invention is that the locking means has a compressible elastic plug for frictionally engaging against an outer surface of the catheter in order to releasably lock the stabilizer in place at a selected position.

Yet another feature of the invention is that the system may have a clamp on the conduit adjacent the sidearm of the connector to releasably close the lumen of the conduit.

A further feature of the invention is that the catheter assembly may have an elastic member on a proximal end of the connector, such that the needle may be passed through the elastic member and connector into the catheter.

Yet another feature of the invention is that the elastic member automatically closes when the needle is removed from the member.

Further features will become more fully apparent in the following description of the embodiments of this invention and from the appended claims.

DESCRIPTION OF THE DRAWINGS

In the drawings:

FIG. 1 is a fragmentary elevational view of a suprapubic catheter system of the present invention;

FIG. 2 is a fragmentary sectional view of a puncture member in the system of FIG. 1;

FIG. 3 is a fragmentary sectional view of a catheter assembly in the system of FIG. 1;

FIGS. 4-7 are fragmentary elevational views illustrating steps during placement of the system in a patient's body;

DESCRIPTION OF THE PREFERRED EMBODIMENTS

Figure 8:
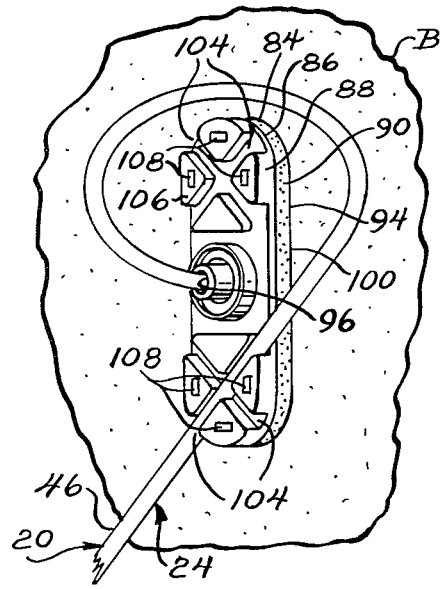
FIG. 8 is a fragmentary perspective view illustrating a further step during placement of the system in a patient's body, with a locking device being omitted for clarity in the drawing.

Referring now to FIG. 1, there is shown a suprapubic catheter system generally designated 20 having a puncture member 22, a catheter assembly 24, a conduit 25, and a drainage receptacle or bag 26. With reference to FIGS. 1 and 2, the puncture member 22 has an elongated needle 28 having a lumen 30, a sharp tip 32 at a distal end 34 of the needle, and a hollow hub 36 attached to a proximal end 38 of the needle 28. As shown, the hub 36 has an annular distal flange 40 with internal threads 42 for a purpose described below. As illustrated in FIG. 1, the puncture member 22 has an indicator mark 44 on the needle 28 for purposes which will also be described below.

With reference to FIGS. 1 and 3, the catheter assembly 24 has an elongated catheter 46 of flexible plastic material having a lumen 48, a distal end portion 50 in the form of a coil 52, and a proximal end 54. As shown, the coil 52 has a plurality of spaced openings 53 communicating with the lumen 48.

The catheter assembly 24 also has a Y-connector 56 having a bore 58 extending therethrough, with a distal end 60 of the connector 56 being attached to the proximal end 54 of the catheter 46. The connector 56 has threads 62 at a proximal end 64 of the connector 56. The connector 56 also has a sidearm 66 having a lumen 68 communicating with the bore 58 of the connector 56.

The catheter assembly 24 also has a plug 70 having a closed tongue 72, and an annular flange 74 having internal threads 76. In use, the plug 70 is secured to the proximal end 64 of the connector 56, with the threads 76 of the plug 70 engaging the threads 62 of the connector 56. In this configuration, the tongue 72 of the plug 70 is received in the bore 58 of the connector 56 in order to close the bore 58.

The catheter assembly 24 has an elongated sleeve 80 having a bore 82 to slidably receive the catheter 46. The sleeve 80 has a length approximately equal to the length of the catheter coil 52.

The catheter assembly 24 also has a stabilizer 84 comprising an elongated plate 86 extending on opposed sides of the catheter 46, with the plate 86 having a proximal sheet 88 of suitable plastic material, and a distal sheet 90 of relatively soft material, such as foam. As shown, the plate 86 has a recess or pocket 92 in a distal surface 94 of the plate 86, with the pocket 92 extending peripherally around an opening 96 in the plate 86 to slidably receive the plate 86 on the catheter 46. As shown, the pocket 92 receives an antiseptic agent 98, such as povidone-iodine, for a purpose which will be described below. The plate 86 has a layer of adhesive 100 on the distal surface 94 of the plate 86, with the adhesive 100 being releasably covered by release sheets 102. With reference to FIGS. 1, 3, and 8, the plate 86 has a pair of cross slits 104 in a proximal surface 106 of the plate 86 on opposed ends or sides of the plate 86. The slits 104 have a width to snugly engage the catheter 46, as will be described below. Also, the plate 86 has a plurality of apertures 108 extending through the plate 86 at spaced locations around the periphery of the plate 86. The proximal sheet 88 of the plate 86 has an annular flange 110 extending proximally from the plate 86.

The catheter assembly 24 also has a locking device 112 received on the catheter 46. The locking device 112 has a cylindrical plug 114 of elastic material having a bore 116 to slidably receive the catheter 46. The locking device 112 also has a body member 118 having a bore 120 to slidably receive the catheter 46. The body member has a distal annular flange 122 which is secured to the flange 110 of the stabilizer 84 by suitable means, such as by threads 124. The body member 118 also has a cavity 126 to snugly receive the plug 114, with the body member 118 having a proximal annular flange 128. As shown, the flange 128 has threads 130 on an outer surface of the flange 128 at a proximal end of the flange 128. The locking device 112 also has a compression member 132 having a distal nipple 134 defining a bore 136 to slidably receive the catheter 46. As shown, the compression member 132 has an annular flange 138 with internal threads 140 which engage with the threads 130 of the body member 118. As shown, the distal end of the nipple 134 slightly engages the plug 114 while the flange 138 is located at a proximal end of the flange 128. In this configuration, the bore 116 of the plug 114 is sufficiently large to permit sliding movement of the plug 114 along the catheter 46, and in this configuration the locking device 112 is released from the catheter 46 in order to permit longitudinal movement of the stabilizer 84 along the catheter 46. However, when the flange 138 is moved distally along the flange 128 through use of the threads 140 and 130, the distal end of the nipple 134 bears against the plug 114 and compresses the plug 114 in order to reduce the size of the plug bore 116. In this configuration, the plug 114 frictionally engages against the outer surface of the catheter 46 in order to releasably lock the locking device 112 and the stabilizer 84 in place at a desired position on the catheter.

With reference to FIGS. 1 and 3, the receptacle 26 has a front wall 150 and a rear wall 152 of flexible plastic material joined about the peripheries of the walls 150 and 152 to define a chamber 154 intermediate the walls 150 and 152. The receptacle 26 also has a hollow connector 156 secured to the front wall 150, such that the connector 156 communicates with the chamber 154 in the receptacle 26. The receptacle 26 may also have a vent 158 of known material which filters bacteria from air, with the vent 158 communicating between the chamber 154 and the atmosphere.

The conduit 25 has a lumen 160, an upstream end 162 secured to the sidearm 66 of the connector 56 with the lumen 160 of the conduit 25 communicating with the lumen 68 of the connector 56, and a downstream end 164 connected to the connector 156 of the receptacle 26 with the lumen 160 of the conduit 25 communicating with the chamber 154 through the connector 156. The conduit 25 has a clamp 166 of known type located on the conduit 25 adjacent the sidearm 66 of the connector 56. The clamp 166 may be moved between a closed position, as shown in FIG. 1 with the clamp 166 closing the lumen 160 of the conduit 25, and an open position, as shown in FIG. 7, with the clamp 166 opening the lumen 160 of the conduit 25. In this manner, the clamp 166 may be used to releasably close the lumen 160 of the conduit 25.

In use of the system 20, the puncture member 22 is initially removed from the catheter assembly 24. The plug 70 is initially placed on the connector 56 with the threads 76 of the plug 70 engaging the threads 62 of the connector 56. As shown in FIG. 1, the stabilizer 84 and locking device 112 of the catheter assembly 24 are located adjacent the proximal end 54 of the catheter 46, and the sleeve 80 is removed from the catheter coil 52.

Also, the clamp 166 is closed about the conduit 25 at a location adjacent the sidearm 66 of the connector 56.

Next, with reference to FIG. 4, the plug 70 is removed from the proximal end 64 of the connector 56. Also, the sleeve 80 is moved over the distal end portion 50 of the catheter 46 in order to straighten the coil 52 of the catheter 46. At this time, with reference to FIG. 5, the puncture member 22 is secured to the catheter assembly 24 with the needle 28 passing through the bore 58 of the connector 58 and the lumen 48 of the catheter 46. As shown, the hub 36 of the puncture member 22 is releasably secured to the proximal end 64 of the connector 56 through use of the threads 42 and 62. In this configuration, the tip 32 of the needle 28 projects slightly from the distal end portion 50 of the catheter 46. After placement of the puncture member 22 on the catheter assembly 24, the sleeve 80 may be removed from the catheter 46, since the sleeve 80 is used to facilitate insertion of the needle 28 into the distal end portion 50 of the catheter 46. At this time, the locking device 112 may be released from the catheter 46, and the stabilizer 84 and locking device 112 may be moved to a distal location on the catheter 46 spaced proximally a slight distance from the distal end portion 50 of the catheter 46, after which the locking device 112 may be actuated in order to lock the locking device 112 and stabilizer 84 in place. After filling the bladder with liquid through use of a urinary catheter, the needle tip 32 may be utilized to puncture the abdominal wall of a patient's body B, with the needle tip 32 and distal end of the catheter 46 passing through the abdominal wall. Once the tip 32 of the needle 28 is located in the patient's bladder, urine will flow through the lumen 30 of the needle 28, and will be visible on the hub 36 of the puncture member 22. Once the beads of urine are seen on the hub 36, the physician knows that the needle tip 32 is located in the patient's bladder. During the puncture procedure of the system 20, the stabilizer 84 facilitates insertion of the needle tip 32 into the patient's body B and the bladder.

Next, with reference to FIG. 6, the locking device 112 is released, and the stabilizer 84 and locking device 112 are moved to a more proximal location on the catheter 46, after which the locking device 112 is actuated in order to lock the stabilizer 84 in place. Also, the hub 36 of the puncture member 22 is released from the connector 56, and the catheter 46 is moved distally along the needle 28 in order to permit placement of the distal end portion 50 of the catheter 46 in the bladder B' of the patient. The catheter 46 is moved distally on the needle 28 until the indicating mark 44 is visible outside the connector 56, as shown. The distance between the hub 36 and the indicating mark 44 is approximately equal to the length of the catheter coil 52. Thus, when the indicating mark 44 is visible, the physician knows that the coil 52 of the catheter 46 is located in the patient's bladder B'. At this time, the puncture member 22 is removed from the catheter assembly 24, and the catheter 46 may be moved distally a further distance into the bladder B', if desired.

Next, with reference to FIG. 7, the plug 70 is secured on the proximal end 64 of the connector 56 in order to close the bore 58 of the connector 56, and prevent passage of urine therethrough. Also, the clamp 166 on the conduit 25 is released in order to permit passage of urine through the conduit 25. The release sheets 102 are removed from the adhesive 100 on the stabilizer 84 in order to expose the adhesive 100. The locking device 112 is released, and the locking device 112 and stabilizer 84 are moved distally along the catheter 46 until the adhesive 100 engages against the patient's body B, such that the adhesive 100 secures the stabilizer 84 to the outside of the patient's body B. At this time, the locking device 112 is actuated in order to lock the locking device 112 and stabilizer 84 against the patient's body B. At this time, urine from the bladder B' drains through the openings 53 in the catheter coil 52, through the lumen 48 of the catheter 46, and through the conduit 25 and connector 156 into the chamber 154 of the receptacle 26 for collection therein. In this manner, urine drains from the bladder B' to the receptacle 26 during catheterization of the patient.

Finally, with reference to FIG. 8, a coil is made in a proximal portion of the catheter 46, and the catheter is snapped into a slit 104 of the stabilizer 84 in order to secure the catheter 46 in place on the stabilizer 84, and direct the proximal end 54 of the catheter 46 toward a side of the patient's body where it communicates through the conduit 25 with the receptacle 26. If desired, strips of adhesive may be placed on the opposed end portions of the stabilizer 84, with the strips being secured to the patient's body B in order to provide additional means for securing the stabilizer 84 to the patient's body B. Also, the tape strip extending over the secured portion of the catheter 46 in the slit 104 additionally insures securement of the catheter 46 to the stabilizer 84.

During catheterization of the patient, the clamp 166 may be closed in order to close the conduit 25. At this time, the plug 70 is removed from the connector 56, and a sample of urine may be obtained through use of a syringe (not shown) attached to the proximal end 64 of the connector 56. Also, the syringe may be utilized to irrigate the catheter and bladder through the connector 56. After the irrigation or sampling procedure has been completed, the plug 70 is reattached to the connector 56, and the clamp 166 is released to permit drainage again to the receptacle 26.

Figure 9:
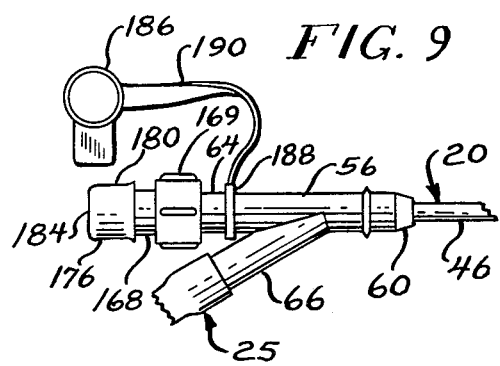
FIG. 9 is a fragmentary elevational view of another embodiment of the system of the present invention.
Figure 10:
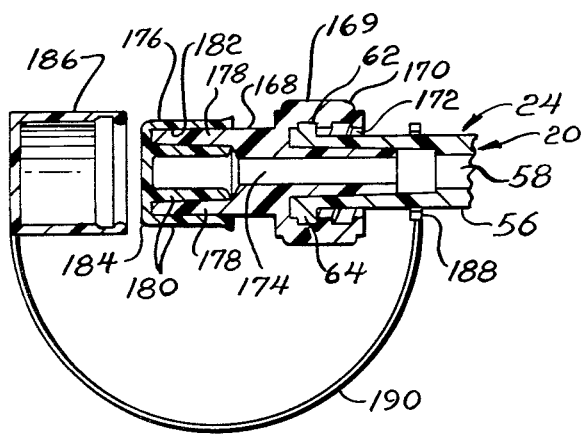
FIG. 10 is a fragmentary sectional view of the system of FIG. 9.
Figure 11:
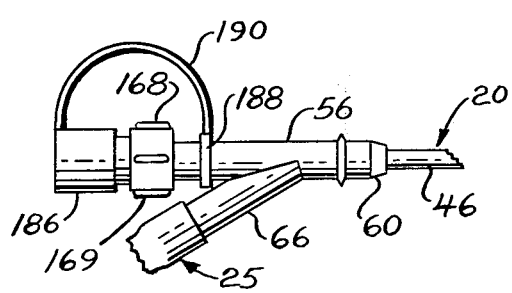
FIG. 11 is a fragmentary elevational view with a cap located over a plug in the system of FIG. 9.

Another embodiment of the present invention is illustrated in FIGS. 9-11, in which like reference numerals designate like parts. In this embodiment, the catheter assembly 24 has a closed plug 168 for releasable attachment to the proximal end 64 of the connector 56. A plug 168 has a body member 169 having a distal annular flange 170 with internal threads 172 for securement of the plug 168 to the threads 62 of the connector 56 in order to releasably secure the plug 168 in place on the connector 56. As shown, the body member 169 has a bore 174 communicating with the bore 58 of the connector 56. Also, the plug 168 has an elastic member 176 secured to a proximal annular flange 178 of the body member 169, with the elastic member 176 having a pair of spaced annular flanges 180 defining an annular groove 182 to receive the flange 178. As shown, the inner flange 180 of the elastic member 176 defines a continuation of the bore 174, and the elastic member 176 has an end wall 184 closing the bore 174. The catheter assembly 24 has a hollow cap 186 of a suitable size for placement over the elastic member 176 of the plug 168. The cap 186 has a ring 188 received on the connector 56, and a strap 190 extending between the cap 186 and ring 188, in order to secure the cap 186 in place on the connector 56.

In use, the cap 186 is removed from the elastic member 176, and the needle 28 of the puncture member 22 is passed through the end wall 184 of the elastic member 176, in order to place the needle 28 in position in the catheter 46. After placement of the system 20 in the patient's body, the needle 28 of the puncture member 22 is removed from the elastic member 176, and the elastic member 176 automatically seals in order to close the opening made by the needle 28 in the end wall 184, and close the bore 174. After removal of the needle 28, the cap 186 is placed over the elastic member 176 in order to prevent contamination or soiling of the elastic member 176 during catheterization. When it is desired to obtain a sample of urine or irrigate the catheter or patient's bladder, the cap 186 is removed from the elastic member 176, and a needle attached to the distal end of a syringe is inserted through the end wall 184 of the elastic member 176 into the bore 174. At this time, a sample of urine may be obtained through use of the syringe once the clamp 166 is closed, or the catheter 46 may be irrigated through use of the syringe by pumping liquid through the syringe needle.

The foregoing detailed description is given for clearness of understanding only, and no unnecessary limitations should be understood therefrom, as modifications will be obvious to those skilled in the art.

I claim:

1. A suprapubic catheter system, comprising:
a puncture member comprising an elongated needle; and
a catheter assembly comprising an elongated catheter having a distal end for placement in a patient, a proximal end, and a lumen to receive the needle, a stabilizer comprising a plate extending on opposed sides of the catheter, with said plate having an opening to slidably receive the plate on the catheter, and means for selectively locking the stabilizer at a desired position on the catheter, said locking means comprising, an elastic plug having a bore to slidably receive the catheter, a body member having a cavity to receive the plug and a bore to slidably receive the catheter, with a distal end of the body member being secured to a proximal side of the stabilizer plate, a compression member having a bore to slidably receive the catheter and a nipple for contacting the plug, and means for adjustably securing the compression member to a proximal end of the body member, such that the compression member may be moved from a first proximal position with the bore of the plug sufficiently large for sliding the plug along the catheter, and a second distal position with the nipple bearing upon the plug to decrease the size of the plug bore in order for the plug to frictionally engage the outer surface of the catheter.

2. The system of claim 1 wherein said stabilizer is elongated.

3. The system of claim 1 wherein the stabilizer has a plurality of spaced apertures extending through the plate for suturing the plate to the patient's body.

4. The system of claim 1 including adhesive on a distal surface of the stabilizer plate.

5. The system of claim 1 wherein said plate has a sheet of foam defining a distal surface of the stabilizer.

6. A suprapubic catheter system, comprising:
a puncture member comprising an elongated needle; and
a catheter assembly comprising an elongated catheter having a distal end for placement in a patient, a proximal end, and a lumen to receive the needle, a stabilizer comprising a plate extending on opposed sides of the catheter, with said plate having an opening to slidably receive the plate on the catheter, and means for selectively locking the stabilizer at a desired position on the catheter, wherein a proximal surface of the stabilizer has slot means extending across the plate, with the slot means being of a size to snugly receive the catheter, and in which the slot means comprises a pair of slots crossing each other on opposed sides of the plate.

* * * * *